US007879625B1

(12) United States Patent
Boss

(10) Patent No.: US 7,879,625 B1
(45) Date of Patent: Feb. 1, 2011

(54) PREPARATION OF SERS SUBSTRATES ON SILICA-COATED MAGNETIC MICROSPHERES

(75) Inventor: Pamela A. Boss, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 14 days.

(21) Appl. No.: 12/326,946

(22) Filed: Dec. 3, 2008

(51) Int. Cl.
G01N 33/553 (2006.01)
B05D 5/00 (2006.01)

(52) U.S. Cl. .............. 436/526; 436/525; 436/518; 436/531; 436/527; 436/532; 436/534; 436/805; 427/2.11; 427/2.13; 427/287; 427/383.1; 427/404

(58) Field of Classification Search .......... 436/526, 436/525, 518, 527, 531, 532, 534, 805; 427/2.11, 427/2.13, 287, 383.1, 404
See application file for complete search history.

(56) References Cited

U.S. PATENT DOCUMENTS

| | | |
|---|---|---|
| 6,174,677 B1 | 1/2001 | Vo-Dinh |
| 6,614,523 B1 | 9/2003 | Boss et al. |
| 6,828,786 B2 | 12/2004 | Scherer et al. |
| 6,888,629 B1 | 5/2005 | Boss et al. |
| 6,947,132 B1 | 9/2005 | Boss et al. |
| 6,967,717 B1 | 11/2005 | Boss et al. |
| 7,022,288 B1 | 4/2006 | Boss |
| 7,116,416 B1 | 10/2006 | Boss et al. |
| 7,135,055 B2 | 11/2006 | Mirkin et al. |
| 7,139,072 B1 | 11/2006 | Boss et al. |
| 7,141,431 B2 | 11/2006 | Chandler et al. |
| 7,147,687 B2 | 12/2006 | Mirkin et al. |
| 7,238,472 B2 | 7/2007 | Mirkin et al. |
| 7,314,711 B2 | 1/2008 | Richter et al. |
| 2002/0061363 A1 | 5/2002 | Halas et al. |
| 2002/0132045 A1 | 9/2002 | Halas et al. |
| 2002/0155507 A1 | 10/2002 | Bruchez et al. |
| 2002/0177143 A1 | 11/2002 | Mirkin et al. |

(Continued)

OTHER PUBLICATIONS

Carron et al., Octadecylthiol-Modified Surface-Enhanced Raman Spectroscopy Substrates: A New Method for the Detection of Aromatic Compounds, Journal, 1992, pp. 1950-1954, vol. 26, Environ. Sci. Technol.

(Continued)

Primary Examiner—Jacob Cheu
Assistant Examiner—Pensee T Do
(74) Attorney, Agent, or Firm—Kyle Eppele; Stephen E. Baldwin

(57) ABSTRACT

Improved surface-enhanced Raman scattering (SERS) substrates comprising chemically-derivatized magnetic microparticles complexed with metal colloidal particles or substrates. The SERS substrates permit collection, detection, measurement, and/or analysis of analytes present at concentrations ranging parts per trillion to parts per billion. Further, compositions, methods, and devices that provide for rapid and/or sensitive detection of chemical compounds of interest present in small concentrations. The subject matter has use in the areas of homeland security and force protection, for example, in the detection of trace samples including, for example, BTEX (benzene, toluene, ethylbenzene, and xylenes), chlorinated solvents, TNT, nerve agents, blister agents, metal ions, anions, antigens, peptides, nucleic acids, spores, fungi, viruses, and bacteria.

17 Claims, 4 Drawing Sheets

U.S. PATENT DOCUMENTS

| | | | |
|---|---|---|---|
| 2003/0129608 | A1 | 7/2003 | Mirkin et al. |
| 2003/0158474 | A1 | 8/2003 | Scherer et al. |
| 2003/0211488 | A1 | 11/2003 | Mirkin et al. |
| 2003/0215865 | A1 | 11/2003 | Mayer et al. |
| 2004/0005582 | A1 | 1/2004 | Shipwash |
| 2004/0023261 | A1 | 2/2004 | Bruchez et al. |
| 2004/0038255 | A1 | 2/2004 | Mirkin et al. |
| 2004/0086897 | A1 | 5/2004 | Mirkin et al. |
| 2004/0128081 | A1 | 7/2004 | Rabitz et al. |
| 2005/0059031 | A1 | 3/2005 | Bruchez et al. |
| 2005/0074779 | A1 | 4/2005 | Vo-Dinh |
| 2005/0130163 | A1 | 6/2005 | Smith et al. |
| 2005/0221333 | A1 | 10/2005 | Sundararajan et al. |
| 2006/0014172 | A1 | 1/2006 | Muller et al. |
| 2006/0211061 | A1 | 9/2006 | Haik |
| 2006/0275757 | A1 | 12/2006 | Lee et al. |
| 2007/0148634 | A1 | 6/2007 | Bruchez et al. |
| 2007/0184970 | A1 | 8/2007 | Gao |
| 2007/0190551 | A1 | 8/2007 | Mirkin et al. |

OTHER PUBLICATIONS

Oleschuk et al., Trapping of Bead-Based Reagents within Microfluid Systems: On-Chip Solid-Phase Extraction and Electrochromatography, Journal, 2000, pp. 585-590, vol. 72, Analytical Chemistry.

Ivo Safarik and Mirka Safarikova, Magnetic Nanoparticles and Biosciences, Journal, 2002, pp. 737-759, vol. 133, Monatshefte fur Chemie Chemical Monthly.

M. Fleischmann et al., Raman Spectra of Pyridine Adsorbed at a Silver Electrode, Journal, 1974, pp. 163-166, vol. 26(2), Elsevier Science Publishers B.V.

Ken Mullen and Keith Carron, Adsorption of Chlorinated Ethylenes at 1-Octadecanethiol-Modified Silver Surfaces, Journal 1994, pp. 478-483, vol. 66, Analytical Chemistry.

Olson et al., Characterization of Silane-Modified Immobilized Gold Colloids as a Substrate for Surface-Enhanced Raman Spectroscopy, Journal, 2001, pp. 4268-4276, vol. 73, Analytical Chemistry.

Storey et al, Electrochemical SERS Detection of Chlorinated Hydrocarbons in Aqueous Solutions, Journal, 1994, pp. 1265-1271, vol. 48, Applied Spectroscopy.

David L. Jeanmaire and Richard P. Van Duyne, Surface Raman Spectroelectrochemistry Part I Heterocyclic, Aromatic, and Aliphatic Amines Adsorbed on the Anodized Silver Electrode, Journal, 1977, pp. 1-20, vol. 84, Journal of Electroanalytical Chemistry.

Keith T. Carron and Brian J. Kennedy, Molecular-Specific Chromatographic Detector Using Modified SERS Substrates, Journal, 1995, pp. 3353-3356, vol. 67, Analytical Chemistry.

Olson et al., C18 Modified Metal-Colloid Substrates for Surface-Enhanced Raman Detection of Trace-Level Polycyclic Aromatic Hydrocarbons in Aqueous Solution, Journal, 2004, pp. 1394-1400, vol. 58, Applied Spectroscopy.

Stroink et al., On-line Sample Preconcentration in Capillary Electrophoresis, Focused on the Determination of Proteins and Peptides, Journal, 2001, pp. 2374-2383, vol. 22, Electrophoresis.

Robin L. Garrell, Surface-Enhanced Raman Spectroscopy, Journal, 1989, pp. 401A-411A, vol. 61, Analytical Chemistry.

Lee et al., Microelectromagnets for the Control of Magnetic Nanoparticles, Journal, 2001, pp. 3308-3310, vol. 79, Applied Physics Letters.

David Ross and Laurie E. Locascio, Microfluidic Temperature Gradient Focusing, Journal, 2002, pp. 2556-2564, vol. 74, Analytical Chemistry.

Carrabba et al., Fiber Optic Raman Chemical Sensors, Journal, 1993, pp. 634-642, vol. 93-7, The Electrochemical Society, Inc.

Unpublished patent application entitled Preparation of Magnetic Capture Matrices for the Extraction of Chemical and Biological Agents (NC 097555), U.S. Appl. No. 12/326,153, filed Dec. 2, 2008; Inventor: Boss, Pamela; assigned to the same assignee as the present 097556 application.

PREPARATION OF SERS SUBSTRATES ON SILICA-COATED MAGNETIC MICROSPHERES

FEDERALLY-SPONSORED RESEARCH AND DEVELOPMENT

This invention (Navy Case No. 097556) is assigned to the United States Government and is available for licensing for commercial purposes. Licensing and technical inquiries may be directed to the Office of Research and Technical Applications, Space and Naval Warfare Systems Center, Pacific, Code 2112, San Diego, Calif., 92152; voice 619-553-2778; email T2@spawar.navy.mil.

BACKGROUND

1. Field

The disclosure relates generally to the field of Raman spectroscopy. More specifically, the disclosure relates to preparation of surface-enhanced Raman scattering (SERS) substrates derivatized to have increased lifetime and affinity for analytes of interest. Such compositions and methods have use in the areas of homeland security and force protection, for example, in the detection of trace samples including BTEX (benzene, toluene, ethylbenzene, and xylenes), chlorinated solvents, TNT, nerve agents, blister agents, metal ions, anions, antigens, peptides, nucleic acids, spores, fungi, viruses, and bacteria.

2. Background of the Subject Matter

The present disclosure generally relates to the field of Raman spectroscopy, and more particularly, to the preparation of surface-enhanced Raman scattering (SERS) substrates derivatized to have increased lifetime and affinity for analytes of interest.

Raman spectroscopy is an emission technique that involves inelastic scattering of incident laser energy and results in spectral peaks that are frequency shifted from the incident energy. The Raman bands arise from changes in polarizability in a molecule during vibration. As a result, virtually all organic molecules display a characteristic Raman emission. Therefore, a Raman sensor would not be limited to a specific class of molecules as is the case for the laser induced fluorescence (LIF) sensor. Raman spectrometry allows the fingerprinting of species present and is structurally specific. The inherently high resolution of Raman spectra often permits the analysis of several components in a mixture simultaneously.

Despite the advantages of Raman spectroscopy over other spectroscopic techniques and the technological advances in the area of Raman spectrometry, Raman spectroscopy is, inherently, an insensitive technique. To achieve detection limits in the low ppm range would require either the use of a multiple pass cell or long acquisition times. In the 1970s, it was discovered that Raman scattering from molecules adsorbed on such noble metals as silver, copper, and gold can be enhanced by as much as $10^6$ to $10^7$ (Fleischmann et al., Chem. Phys. Lett., 26:163 (1974); Jeanmaire et al., J. Electroanal. Chem., 84:1 (1977).) This phenomenon, called surface enhanced Raman spectroscopy (SERS), is still not understood despite intensive theoretical and experimental research. It is believed that more than one mechanism is involved in the SERS phenomenon. Initially, the SERS technique was used as a means to probe adsorption at metal interfaces both in electrochemical and gas-phase environments. This technique has proven useful in deducing the effects of interfacial structure and reactivity on the adsorption process, and the sensitivity of the technique as well as its exceptional spectral selectivity has made SERS attractive for a broad range of analytical applications. Garrell, Anal. Chem., 61:401A (1989). SERS can be used for trace organic analysis and as a detection method in gas chromatography, liquid chromatography, and thin layer chromatography. Electrochemical SERS (Carrabba, et al., Fiber Optic Raman Chemical Sensors, in Proceedings of the Symposium on Chemical Sensors A. Riccio and N. Yammazoe, Eds., The Electrochemical Society, Pennington, N.J., p. 634 (1993); Storey, et al., Appl. Spectrosc., 48:1265 (1994)) and SERS of chemically modified surfaces (Canon, et al., Environ. Sci. Technol., 26:1950 (1992); Mullen et al., Anal. Chem., 66:478 (1994)) may be used to detect aromatic compounds and chlorinated hydrocarbons, organic contaminants of environmental concern, in the ppm concentration range.

The SERS technique requires intimate contact between the SERS active surface and analyte. In turn, this requires that the analyte bond to the SERS active surface. Current SERS substrate configurations allow detection limits in the upper ppb to low ppm concentration range. However, there may be requirements for detection limits in the low ppb to high pptr concentration range. Further, SERS substrates readily become poisoned by chemical reactions and result in decreased sensitivity and reliability for detecting Raman scattering due to excitation of the analyte of interest.

Therefore, a need exists for a SERS substrate that minimizes poisoning by chemical reactions and/or increases the lifetime of a SERS substrate's sensitivity and reliability. A means of preparing robust SERS substrates that could be used to detect analytes in the pptr-ppb concentration range would result in a sensing capability that could be used to monitor analytes in real time and in-situ. Besides environmental monitoring, such a sensor could be used for homeland security and force protection. There is a real concern that terrorists could poison water supplies using readily available toxic industrial chemicals such as the BTEX compounds, chlorinated solvents, and anions such as nitrate and perchlorate.

SUMMARY

The present disclosure provides a SERS-active magnetic microparticle, comprising: (a) a silica-coated magnetic microparticle; (b) SERS active colloidal particles immobilized on the surface of the magnetic microparticle; (c) a silica coat encapsulating both the at least one colloidal particle and the magnetic microparticle; and (d) at least one functional siloxane group bound to the silica coat, wherein the functional siloxane group comprises at least one chemical moiety that attracts or binds to an analyte of interest or a group of analytes of interest. The present disclosure also provides a chemical detection sensor system, comprising the SERS-active magnetic microparticles described herein. Furthermore, the present disclosure also provides a method of detecting an analyte of interest in a sample, comprising: (a) contacting the sample with a population of the magnetic microparticles described herein wherein the functional siloxane group of the magnetic microparticles comprises at least one chemical moiety that attracts or binds to the analyte of interest; (b) applying a magnet or magnetic field to the sample so that a magnetic particle fraction can be concentrated at a surface or in a localized volume; (c) analyzing a portion of the magnetic particle fraction with SERS, wherein SERS produces a quantitative signal when the specific analyte is present in the sample; and (d) detecting the presence or absence of the analyte's quantitative signal in the analyzed portion.

BRIEF DESCRIPTION OF THE DRAWINGS

FIG. 4 shows photograph images of an example of magnetic microspheres in solution before (left image) and after (right image) application of a magnetic field.

DETAILED DESCRIPTION

Overview

Figure 1:
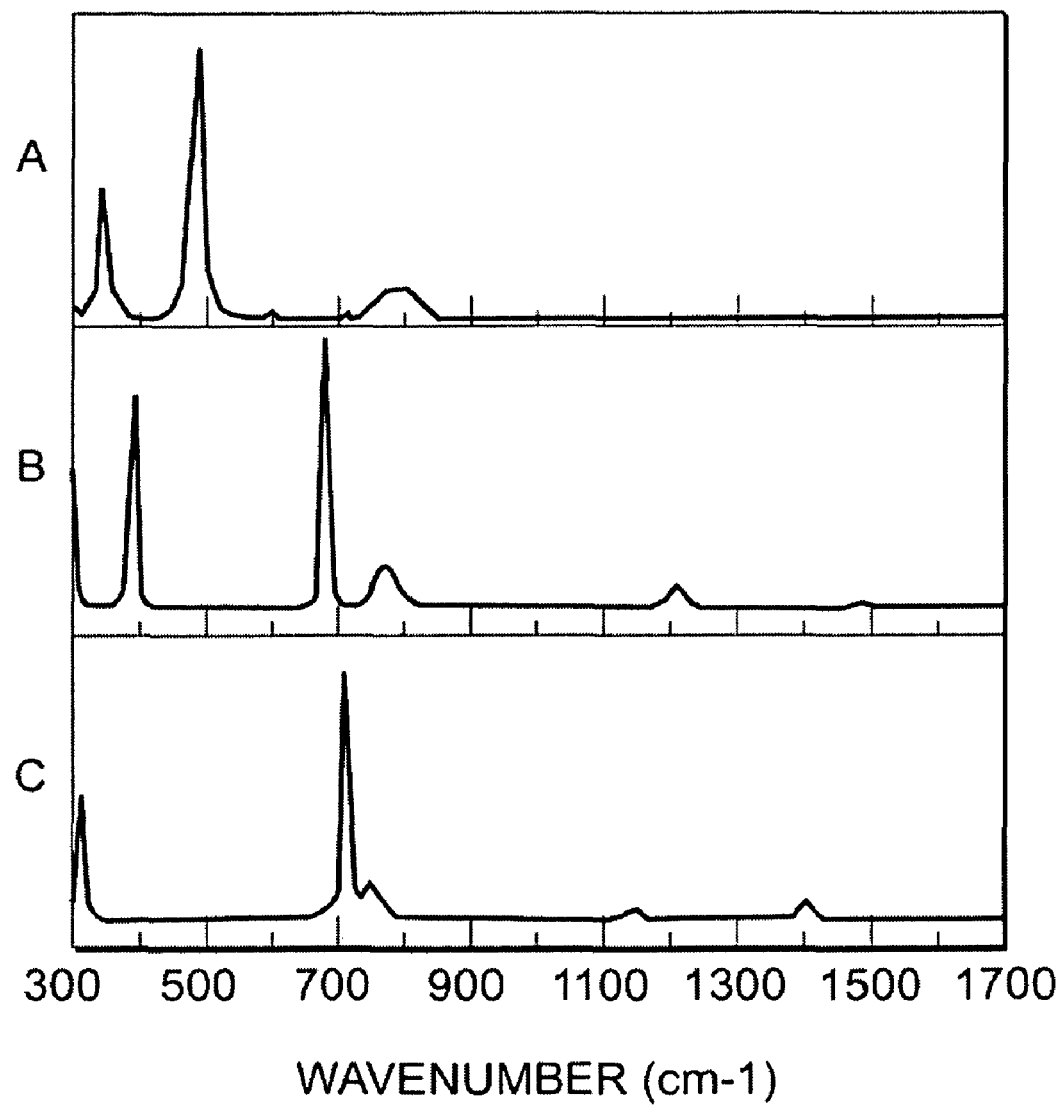
FIG. 1 shows an example of Normal Raman spectra of (A) carbon tetrachloride, (B) chloroform, and (C) methylene chloride. These chlorinated solvents vary in the number of hydrogen and chlorine atoms. Yet they can easily be distinguished by their Raman spectra. Unlike fluorescence, the Raman peaks are very narrow. The inherently high resolution of Raman spectra often permits the analysis and identification of several components in a mixture simultaneously.

This disclosure generally relates to improved surface-enhanced Raman scattering (SERS) substrates comprising chemically-derivatized magnetic microparticles complexed with silver or gold particles or nanostructures. The SERS substrates permit collection, detection, measurement, and/or analysis of analytes present at concentrations ranging in parts per trillion to parts per billion. Further, this disclosure relates generally to compositions, methods, and devices for rapid and/or sensitive detection of chemical compounds of interest present in small concentrations. Such a disclosure has use in the areas of homeland security and force protection, for example, in the detection of trace samples including, for example, BTEX (benzene, toluene, ethylbenzene, and xylenes), chlorinated solvents, TNT, nerve agents, blister agents, metal ions, anions, antigens, peptides, nucleic acids, spores, fungi, viruses, and bacteria.

In one embodiment, the SERS-active magnetic microparticle, comprises: (a) a silica-coated magnetic microparticle; (b) SERS active colloidal particles immobilized on the surface of the magnetic microparticle; (c) a silica coat encapsulating both the colloidal particles and the magnetic microparticle; and (d) at least one functional siloxane group bound to the silica coat, wherein the functional siloxane group comprises at least one chemical moiety that attracts or binds to an analyte of interest or a group of analytes of interest. The colloidal particles are metal colloidal particles wherein the metal is selected from the group consisting of silver, gold, copper, and combinations thereof. The colloidal particles are immobilized on the surface of the magnetic microparticle by binding to, for example, amine groups that are bound to the magnetic microparticle. At least one functional siloxane group, selected from the group consisting of cationic siloxanes, anionic siloxanes, aliphatic siloxanes, aromatic siloxanes, and combinations thereof, is bound to the silica coat of the magnetic microparticle. The colloidal particles have mean diameters ranging from 10 nm to 100 nm. The silica-coated magnetic microparticle has a mean diameter ranging from 1 um to 10 um, prior to immobilizing the colloidal particles on its surface.

The present disclosure also provides a chemical detection sensor system, comprising the SERS-active magnetic microparticles described herein. In one approach, the chemical detection sensor system comprises a support structure supporting the SERS-active magnetic microparticles, wherein each SERS-active magnetic microparticle is disposed to undergo a chemical reaction and a state change in the presence of an analyte; a magnet or magnetic field for concentrating the SERS-active magnetic microparticles; a chemical reaction sensor disposed to detect said state change; a processor operably coupled to said chemical reaction sensors and disposed to record said state change; and a power source disposed to energize said processor.

Furthermore, the present disclosure also provides a method of detecting an analyte of interest in a sample, comprising: (a) contacting the sample with a population of the magnetic microparticles described herein wherein the functional siloxane group of the magnetic microparticles comprises at least one chemical moiety that attracts or binds to the analyte of interest; (b) applying a magnet or magnetic field to the sample so that a magnetic particle fraction can be concentrated at a surface or in a localized volume; (c) analyzing a portion of the magnetic particle fraction with SERS, wherein SERS produces a quantitative signal when the specific analyte is present in the sample; and (d) detecting the presence or absence of the analyte's quantitative signal in the analyzed portion. In one embodiment, the method further comprises calculating the concentration of the specific analytes in the sample by comparing the analyte detection signal to signals obtained for a standard curve of samples having a known concentration of analyte. In another approach, the analyte detected is present in the original sample at a concentration ranging from 1 part per trillion to 100 parts per billion. In still other examples, the analyte detected is selected from the group consisting of benzene, toluene, ethylbenzene, xylenes, chlorinated solvents, TNT, nerve agents, blister agents, anions, cations, metal ions, anions, antigens, peptides, nucleic acids, spores, fungi, viruses, and bacteria. In further embodiments, the chemical analyte to be detected is not a biological molecule. "Biological molecule" as used herein means any class of organic molecule normally found in living organisms such as, for example, antigens, carbohydrates, peptides, nucleic acids, and including organic molecules normally found in spores, fungi, viruses, or bacteria. In another example, the method is performed with the sample present inside a MEMS device. In yet other embodiments, the complex of magnetic microparticle bound to analyte is further contacted with a labeling reagent specific for an analyte of interest; wherein reaction of the reagent with the analyte permits improved detection of the analyte of interest, such as, for example, the labeling reagent specific for an analyte of interest comprises a fluorescence marker, a radioisotope marker, or a spectroscopic marker.

There are several methods to prepare silver/gold colloids.

Example 1

SERS substrates were prepared and evaluated. The substrates consisted of colloidal Ag, chemically etched Ag foils, electrochemically etched Ag and Au electrodes, and Au films on glass substrates. The Ag and Au were reacted with organic thiols to form a self-assembled monolayer (SAM). The thiol coating protects the SERS substrate from poisoning thereby increasing the lifetime of the SERS substrate from minutes or hours to months. Coatings were chosen which have an affinity for the analyte of interest. Analyte partitions onto the coating and was detected by SERS. The spectral peaks of the analyte directly correspond with those of the neat compound facilitating species identification. These coated SERS substrates can be used to detect contaminants in both the vapor and aqueous phases.

Example 2

Silica-coated, amine terminated magnetic microparticles were commercially available (Bioclone, Inc., San Diego, Calif.) or may be manufactured, in which the magnetic core is surrounded by a silane coating. With these magnetic microparticles, sol-gel techniques were used to fabricate SERS-active magnetic microparticles. Specifically, after immobilization of the noble metal colloidal particles, the magnetic microparticles were reacted with a functionalized silane that binds to the silane coating of the magnetic microparticles thereby encapsulating the immobilized colloidal particles. The functional group of the functionalized silane was chosen to attract analytes of interest. The derivatized silver/gold colloidal particles immobilized on magnetic microspheres can be used to capture small quantities of analyte in a large volume. After capture, a magnet was used to draw the magnetic microspheres onto an optical surface where the analyte was detected/speciated by its characteristic SERS response. FIG. 1 shows Raman spectra obtained for (A) carbon tetrachloride (CCl4), (B) chloroform (CHCl3), and (C) methylene chloride (CH2Cl2). These chlorinated solvents vary in the number of hydrogen and chlorine atoms, yet they can easily be distinguished by their Raman spectra. Unlike fluorescence, the Raman peaks were very narrow. The inherently high resolution of Raman spectra often permits the analysis and identification of several components in a mixture simultaneously. Using this approach, compounds can be detected in the low ppb (part per billion) to upper pptr (part per trillion) concentration range. The compounds that can be detected include BTEX (benzene, toluene, ethylbenzene, and xylenes), chlorinated solvents, TNT, nerve agents, blister agents, etc. Such a device has use in the areas of homeland security and force protection.

Example 3

One technique to prepare gold colloid was to put 100 mL of an aqueous 0.01% HAuCl4 solution on a round bottom flask with a stir bar and condenser column. The solution was brought to a boil and, with constant stirring, 1% sodium citrate was added. The amount of sodium citrate controls the size of the gold particles making up the colloid. Addition of 0.42 mL of 1% citrate creates gold particles that average 98 nm in diameter while 0.933 mL creates on average 60 nm size gold particles. The colloid was allowed to reflux for 40 min. One technique to create silver colloid was to put 18 mg silver nitrate in 200 mL water in a round bottom flask with a stir bar and condenser tube. After boiling 4 mL of 1% sodium citrate was added with constant stirring. The colloidal suspension was allowed to reflux for one hr.

The silver/gold colloids prepared in the techniques above may be further concentrated. In one approach, this was done by centrifugation. The final volume of the colloid was decreased from 100 mL to 3 mL—a concentration factor of—33 times.

Example 4

Figure 2:
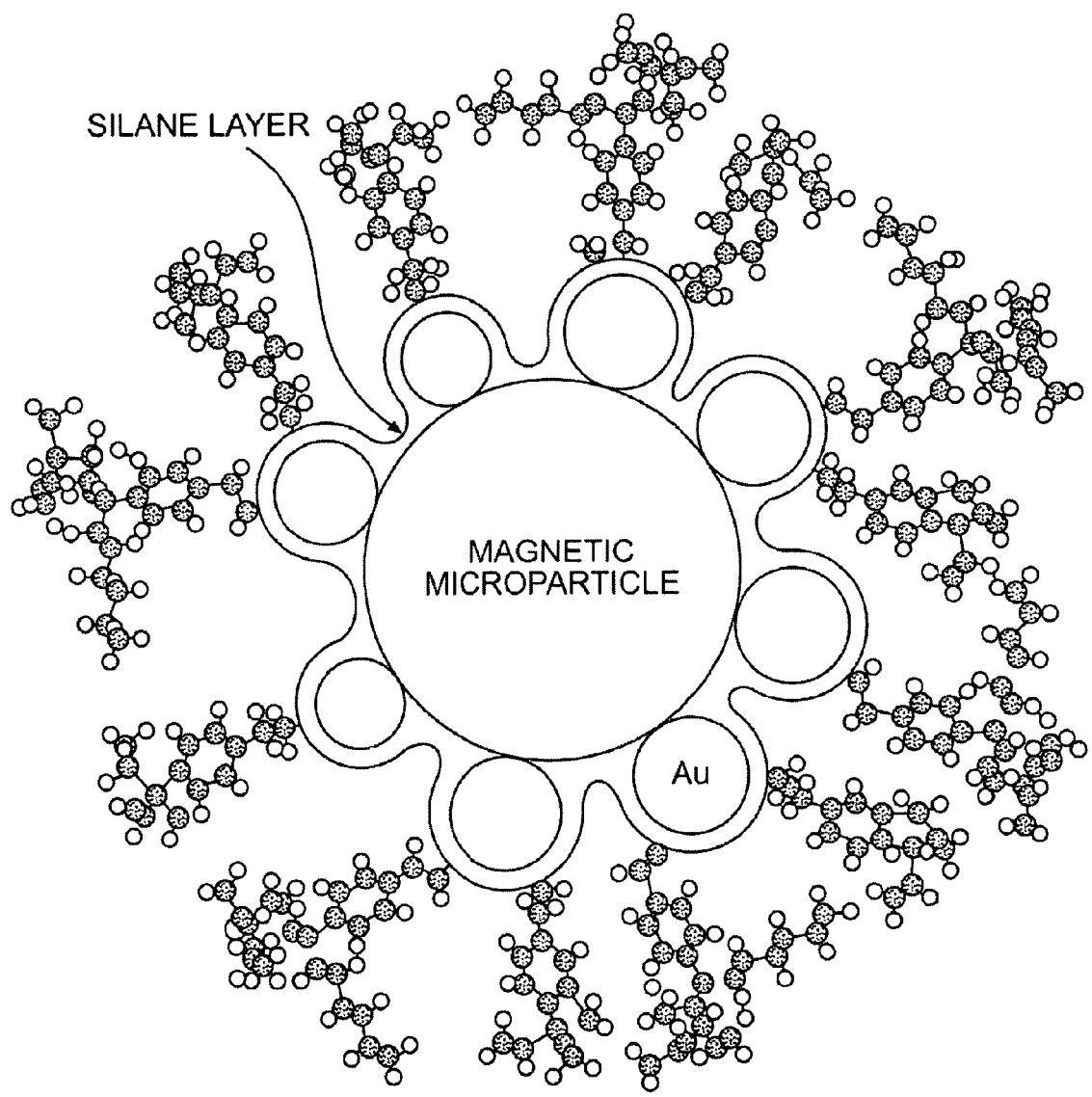
FIG. 2 shows a schematic of an example of gold colloidal particles immobilized on a silica-coated magnetic microparticle having amine-terminated groups.
Figure 3:
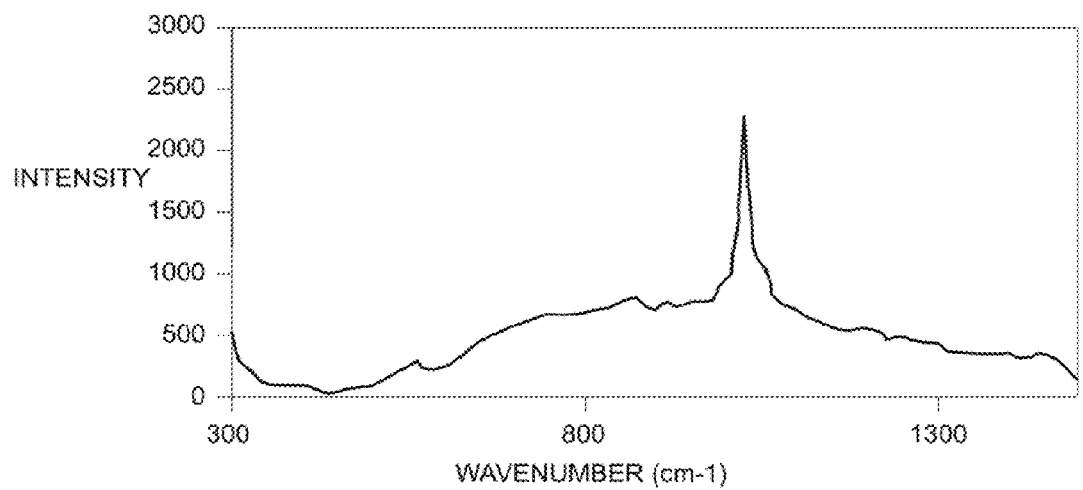
FIG. 3 shows the SERS spectrum obtained for an example of gold colloid immobilized on magnetic microspheres that had been derivatized with ((chloromethyl)phenylethyl)-trimethoxysilane.

SERS-active capture matrices may be prepared using silica-coated, amine terminated magnetic microparticles. Olson et al. demonstrated that silane-modified immobilized gold colloids could be used as SERS substrates. Olson, et al., Anal. Chem., 73:4268 (2001) These substrates were prepared by immobilizing gold colloid onto glass slide that had been derivatized with 3-aminopropyltrimethoxysilane. Afterward a C-18 alkane chain was self-assembled and cross-linked on the immobilized gold colloid surface to encapsulate the colloidal particles thereby producing a stable, hydrophobic SERS substrate. Use of substrates of this type to detect pyrene by the SERS technique was demonstrated. Olson, et al. Appl. Spectrosc., 58:1394 (2004). These substrates were shown to be robust. They exhibited great stability with time and upon exposure to laser irradiation, were reproducible to fabricate, and did not lose their SERS activity upon heating. Similar substrates can be prepared using the Bioclone, Inc. silica-coated, amine-terminated, magnetic microparticles. Another advantage to this approach was that there are commercially available a large number of siloxanes that can be used to create analyte-selective films. Numerous other silane coupling agents known in the art can be used besides siloxanes to encapsulate the silver/gold colloidal particles immobilized on the magnetic microparticle. These siloxanes may be used to modify surfaces for use in chromatography, fabrication of liquid crystal displays, micro-contact printing, and other soft lithography methods. One company that provides a large number of siloxanes was Gelest Inc. in Morrisville Pa. The amine groups of the Bioclone Inc. silica-coated amine-terminated magnetic microparticles were used to immobilize gold or silver colloidal particles. After immobilization of the colloids, the silica coating of the magnetic microparticle were reacted with another siloxane to encapsulate the colloidal particles, as shown in FIG. 2. The functional group of the second siloxane was chosen to attract the analyte of interest. For example, cationic siloxanes can be used to attract anions. The functional group of the second siloxane may also increase the binding affinity of the substrate to the analyte of interest. Aliphatic and aromatic siloxanes can be used to attract chlorinated solvents and BTEX (benzene-toluene-ethylbenzene-xylenes). To obtain a SERS spectrum, a magnet or magnetic field was used to concentrate the magnetic particles onto an optical surface. FIG. 3 shows the SERS spectrum obtained for a gold colloid immobilized on magnetic microspheres that had been derivatized with ((chloromethyl)phenylethyl)-trimethoxysilane.

Figure 4:
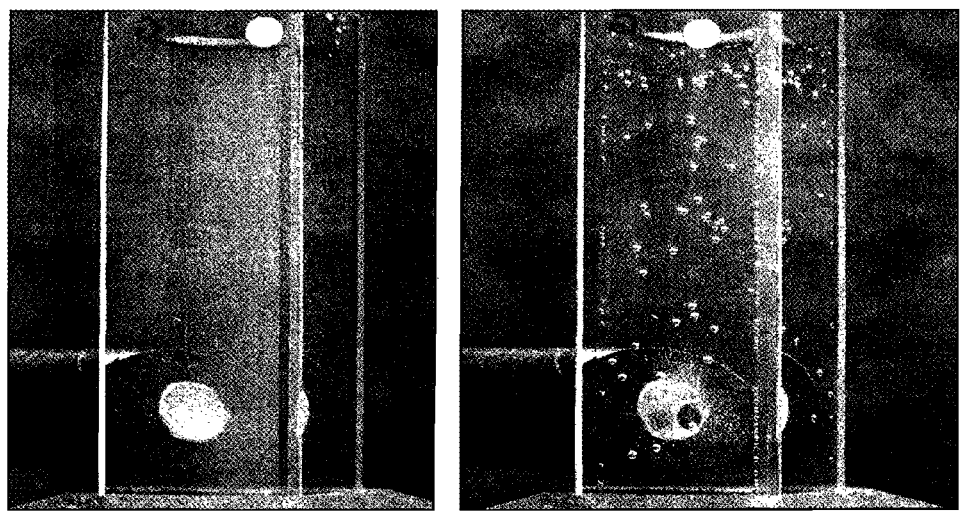
FIG. 4 shows an example of how efficiently a magnet separates the magnetic microspheres from a sample.
Figure 5:
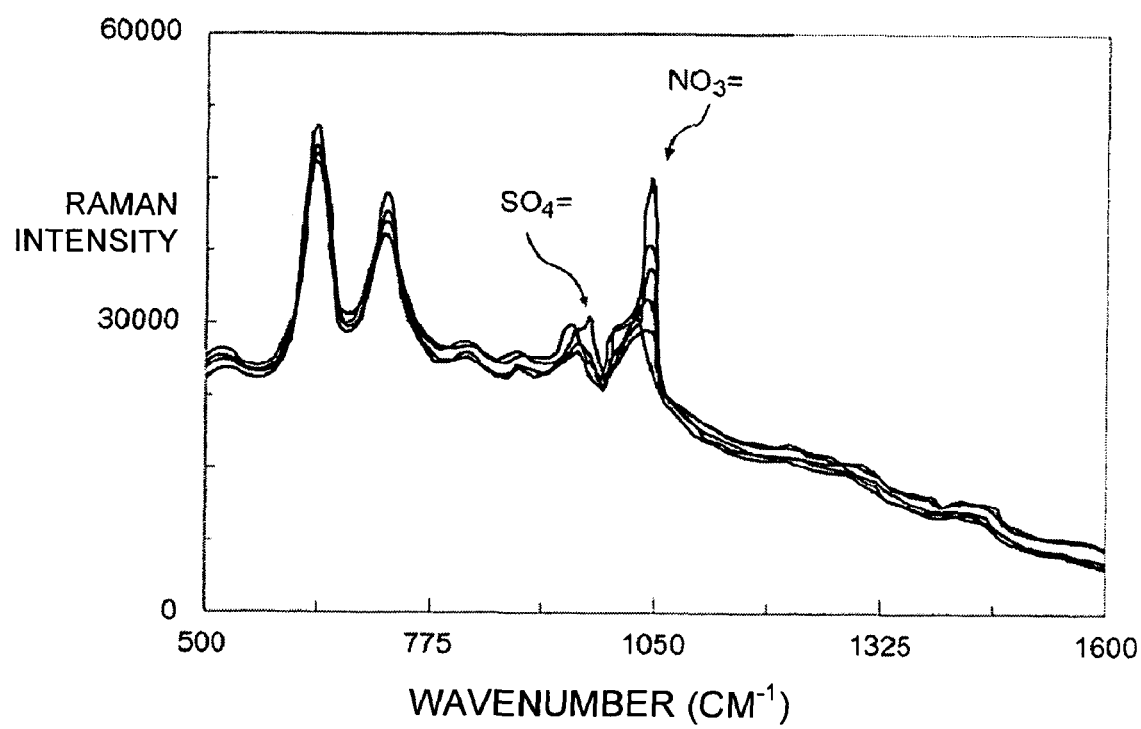
FIG. 5 shows an example of SERS spectra of cysteamine on silver in a sample containing nitrate and sulfate. The Raman emissions due to sulfate and nitrate can be clearly seen in the SERS spectrum of the coating.

The derivatized silver/gold colloid-immobilized magnetic microspheres were used to concentrate an analyte and allow its detection/speciation using the SERS technique. In practice, an aliquot (on the order of 50 uL) of colloid-immobilized magnetic microspheres was pipetted into a sample (volume 50-100 mL). The sample was either rolled, sonicated, or vortexed to keep the magnetic particles suspended and in constant contact with the sample. The coating on the colloidal particles binds to the analyte. After a given amount of time to assure capture of all the analyte present in the sample by the coating (usually 10-20 min), a magnet was used to separate the magnetic microspheres from the sample. FIG. 4 shows an example of how efficiently a magnet separates the magnetic microspheres from a sample. FIG. 4 shows photograph images of an example of magnetic microspheres in solution before (left image) and after (right image) application of a magnetic field. The magnetic microspheres were rinsed to remove any residual sample. Once concentrated onto an optical surface, the magnetic microspheres were excited with a laser and the Raman emissions were collected, transmitted to the spectrometer for dispersion, and the Raman lines detected by a charge coupled device (CCD). The analyte was identified by its characteristic Raman emissions which were distinct from those of the coating. FIG. 5 shows SERS spectra of cysteamine on silver in a sample containing nitrate and sulfate. The Raman emissions due to sulfate and nitrate can be clearly seen in the SERS spectrum of the coating.

Depending upon the physiochemical properties of the analyte and coating and the volume of the sample, analyte can be concentrated 100-10,000 fold. This will result in detection limits in the lower ppb to upper pptr concentration range. For example, detection limits might be obtained ranging from 10 ppb down to 100 pptr The stronger the interaction between the coating and the analyte, the less reversible the reaction becomes. Therefore, for many cases, these derivatized colloid immobilized magnetic microspheres were single use.

The SERS substrates of the present disclosure have many advantages, including: amine-modified and silica coated magnetic microspheres of the present disclosure are commercially available and are inexpensive. Silver/gold colloids are easy to prepare and are inexpensive. Immobilization of the silver/gold colloids on the amine-modified magnetic microspheres was rapid. Immobilized silver/gold colloids can be encapsulated by reacting them with siloxanes to form a thin polymer film. The siloxane coating on the colloid has a characteristic SERS spectrum that can be used for calibration purposes. Siloxanes are chosen that have an affinity for a certain class of compounds. Although colloids have fairly long shelf-lives, the encapsulating siloxane coating on the colloids further protects the SERS surface from degradation thereby extending the usable lifetime of the colloids. The resultant derivatized silver/gold colloids immobilized on magnetic microspheres are easy to manufacture and are inexpensive. The derivatized silver/gold colloids immobilized on magnetic microspheres act as both a preconcentrator and a transducer. When added to a sample and mixed, analyte binds to the derivatized SERS surface. The interaction with the coating on the SERS surface concentrates the analyte onto the magnetic microspheres. A magnet efficiently separates the magnetic microspheres from the rest of the sample. Concentration factors are on the order of 100 to 10,000. Detection limits are in the upper pptr to low ppb concentration ranges. Once the magnetic microspheres are concentrated onto an optical surface, the analyte was detected and speciated by the SERS technique. The silver/gold colloids immobilized on magnetic microspheres are for single use only. Silver/gold colloids that may be encapsulated using a siloxane layer exhibit greater thermal and chemical stability and are also stable upon exposure to laser irradiation.

Substrates of the present disclosure also comprise colloidal Ag, Au, or Cu In some examples, the Ag and Au were reacted with organic thiols to form a self-assembled monolayer (SAM). In this approach, for example, the thiol coating protects the SERS substrate from poisoning thereby increasing the lifetime of the SERS substrate from minutes or hours to months. Coatings may be chosen which have an affinity for the analyte of interest. In general, the analyte partitions onto the coating and is then detected by SERS. In some embodiments, the spectral peaks of the analyte directly correspond with standardized controls of reference compounds facilitating species identification. These coated SERS substrates can be used to detect contaminants in both the vapor and aqueous phases.

Microparticles and nanoparticles can comprise solid metal of nanoscale size or nanoparticles coated with metal layers. Nanospheres of dielectric materials coated with a thin layer of silver (metal nanoshell) have been found to be SERS active. Nanospheres of magnetic materials coated with a thin layer of metal can also be used as SERS-active magnetic nanoparticles. The core diameter and the metal thickness of nanoshells can be varied to modify the SERS properties of the nanoparticles as disclosed in Moody, et al., "Investigation of Experimental Parameters for Surface-Enhanced Raman Spectroscopy," Appl. Spectrosc., 41: 966 (1987).

The derivatized SERS-active magnetic microparticles can be used in conjunction with MEMS devices to decrease sample size, increase speed of analysis, decrease cost and time, and increase sensitivity. One of the biggest challenges faced MEMS devices; is the detection of very dilute solutions of analyte in ultrasmall volumes. Ross D., et al., "Microfluidic Temperature Gradient Focusing", Anal. Chem., 74: 2556-2564 (2002). Consequently, techniques for extracting and concentrating trace amounts of chemical species from a complex environmental sample are needed. Current techniques have used affinity ligands bound to either membranes, silica particles, latex beads, or directly to channel or capillary walls of the device. These techniques require the use of multiple buffers/solvents—one to deliver sample to the preconcentrator and a second to release the sample for analysis. Because of their small dimensions, magnetic capture matrices should prove to be ideal preconcentrators for MEMS devices.

The magnetic capture matrices can be used in conjunction with other spectroscopic techniques besides SERS as well as electrochemical and chromatographic techniques. A variety of chemical substituents may be derivatized onto the surface of magnetic microparticles Nonlimiting examples of such chemical substituents may be selected from the group consisting of amine and carboxyl. Chemical affinity ligands can be grafted directly onto the amine and carboxyl groups on the surface of the magnetic microparticles to create capture matrices that can be used to preconcentrate analytes prior to detection by electrochemical, chromatographic, and optical techniques. The grafting of chemical affinity ligands can be accomplished using the binding chemistries that have been developed previously to bind biological recognition molecules to the magnetic microparticles. In one approach, the amine functional group on the magnetic microparticle is activated by reacting it with glutaraldehyde. Once activated, the magnetic microparticle can bind to a ligand containing, for example, a primary amine group. In another example, the carboxyl group is activated by reaction with EDC, N-(3-dimethylaminopropyl)-N'-3 ethylcarbodiimide HCl, and NHS, hydroxysuccinimide. The activated carboxyl group can then bind to ligands containing, for example, amine, thiol, aldehyde, or carboxyl groups. Other chemistries that can be used to bind chemical affinity ligands to the magnetic microparticles include hydroxyl, hydrazide, chloromethyl, and epoxy. However, magnetic microparticles with these functional groups are not as readily available as those with the amine and carboxyl functional groups. Bioclone, Inc. (San Diego, Calif.) offers silica-coated magnetic microparticles. In the case of these microparticles, the silica coating can be reacted with chemical affinity ligands containing siloxane and other silane coupling groups.

Chemical affinity ligands are chosen to attract the analyte of interest. For example, cationic ligands can be used to attract anions. Aliphatic and aromatic ligands can be used to attract chlorinated solvents and BTEX (benzene-toluene-ethylbenzene-xylenes). There are also EDTA-like ligands that can be used to bind transition metal ions.

In one approach, an aliquot (on the order of 50 uL) of chemically-derivatized magnetic microspheres is pipetted into a sample (volume 50-100 mL). The sample is either rolled, sonicated, or vortexed to keep the magnetic particles suspended and in constant contact with the sample. The chemical affinity ligand on the magnetic microparticles binds to the analyte. After a given amount of time to assure capture of all the analyte present in the sample by the ligand (usually 10-20 min), a magnet is used to separate the magnetic microspheres from the sample. The magnetic microspheres are optionally rinsed to remove any residual sample. Once concentrated onto a surface, the analyte bound to the magnetic microspheres is detected by either spectroscopic, electrochemical, or chromatographic means. Depending upon the physiochemical properties of the analyte and coating and the volume of the sample, analyte can be concentrated 100-10,000 fold. This will result in detection limits in the lower ppb to upper pptr concentration range. The stronger the interaction between the coating and the analyte, the reaction is less reversible. Therefore, for many cases, these derivatized colloid immobilized magnetic microspheres are single use.

CONCLUSION

It will be understood that many additional changes in the details, materials, steps and arrangement of parts, which have been herein described and illustrated to explain the nature of the invention, may be made by those skilled in the art within the principal and scope of the invention as expressed in the appended claims.

What is claimed is:

1. A surface-enhanced Raman scattering-(SERS)-active magnetic microparticle, comprising:
   (a) a magnetic microparticle having a first silica coat;
   (b) colloidal particles immobilized on a surface of the magnetic microparticle;
   (c) a second silica coat encapsulating both the colloidal particles and the magnetic microparticle; and
   (d) at least one functional siloxane group bound to the second silica coat, wherein the functional siloxane group comprises at least one chemical moiety that attracts or binds to an analyte of interest or a group of analytes of interest.

2. The SERS-active magnetic microparticle of claim 1, wherein the colloidal particles are a metal colloidal particles wherein the metal is selected from the group consisting of silver, gold, copper, and combinations thereof.

3. The SERS-active magnetic microparticle of claim 1, wherein the colloidal particles are immobilized on the surface of the magnetic microparticle.

4. The SERS-active magnetic microparticle of claim 1, wherein the colloidal particles is immobilized on the magnetic microparticle by binding to amine groups that are bound to the magnetic microparticle.

5. The SERS-active magnetic microparticle of claim 1, wherein the at least one functional siloxane group bound to the second silica coat is selected from the group consisting of aromatic siloxanes and heterocyclic siloxanes.

6. The SERS-active magnetic microparticle of claim 1, wherein the at least one colloidal particle has a mean diameter ranging from 10 nm to 100 nm.

7. The SERS-active magnetic microparticle of claim 1, wherein the silica-coated magnetic microparticle has a mean diameter ranging from 1 um to 10 um, prior to immobilizing the colloidal particles on its surface.

8. A chemical detection sensor system, comprising:
   SERS-active magnetic microparticles of claim 1;
   a support structure supporting the SERS-active magnetic microparticles, wherein each SERS-active magnetic microparticle is disposed to undergo a chemical reaction and a state change in the presence of an analyte;
   a magnet or magnetic field for concentrating the SERS-active magnetic microparticles;
   a chemical reaction sensor disposed to detect said state change; a processor operably coupled to said chemical reaction sensors and disposed to record said state change; and a power source disposed to energize said processor.

9. A method of detecting an analyte of interest in a sample, comprising:
   (a) contacting the sample with a population of the magnetic microparticles of claim 1 wherein the functional siloxane group of the magnetic microparticles of claim 1 comprises at least one chemical moiety that attracts or binds to the analyte of interest;
   (b) applying a magnet or magnetic field to the sample so that a magnetic particle fraction can be concentrated at a surface or in a localized volume;
   (c) analyzing a portion of the magnetic particle fraction with SERS, wherein SERS produces a quantitative signal when the specific analyte is present in the sample; and
   (d) detecting the presence or absence of the analyte's quantitative signal in the analyzed portion.

10. The method according to claim 9, wherein the method further comprises calculating the concentration of the specific analytes in the sample by comparing the analyte detection signal to signals obtained for a standard curve of samples having a known concentration of analyte.

11. The method according to claim 9, wherein the analyte is detected is present in the original sample at a concentration ranging from 1 part per trillion to 100 parts per billion.

12. The method according to claim 9, wherein the analyte detected is selected from the group consisting of benzene, toluene, ethylbenzene, xylenes, chlorinated solvents, TNT, nerve agents, blister agents, anions, cations, metal ions, anions, antigens, peptides, nucleic acids, spores, fungi, viruses, and bacteria.

13. The method according to claim 9, wherein the method is performed with the sample present in a MEMS device.

14. The method of claim 9, wherein complex of magnetic microparticle bound to analyte is further contacted with a labeling reagent specific for an analyte of interest; wherein reaction of the reagent with the analyte permits improved detection of the analyte of interest.

15. The method of claim 14, wherein the labeling reagent specific for an analyte of interest comprises a fluorescence marker, a radioisotope marker, or a spectroscopic marker.

16. The method of claim 15, wherein the analyte is detected by other spectroscopic techniques besides SERS.

17. The method of claim 15, wherein the analyte is detected by electrochemical or chromatographic techniques.

* * * * *